United States Patent [19]

Hartness

[11] 4,292,839
[45] Oct. 6, 1981

[54] CROWN RELEASE PRESSURE TESTER

[75] Inventor: Thomas S. Hartness, Greenville, S.C.

[73] Assignee: Hartness International, Inc., Greenville, S.C.

[21] Appl. No.: 71,864

[22] Filed: Sep. 4, 1979

[51] Int. Cl.³ ............................................. G01M 3/32
[52] U.S. Cl. ...................................... 73/49.2; 73/49.8
[58] Field of Search ............... 73/49.2, 52, 45.5, 49.3, 73/49.8

[56] References Cited

U.S. PATENT DOCUMENTS

| | | | |
|---|---|---|---|
| 1,211,942 | 1/1917 | Hoff | 73/52 |
| 1,539,937 | 6/1925 | Cochrane | 73/52 |
| 3,035,435 | 5/1962 | Johnson | 73/40 |
| 3,164,979 | 1/1965 | Siegel | 73/4 |
| 3,251,218 | 5/1966 | Russell | 73/52 |
| 3,958,448 | 5/1976 | Willis et al. | 73/37 |
| 4,048,845 | 9/1977 | Gilbert | 73/45.5 |

*Primary Examiner*—Daniel M. Yasich
*Attorney, Agent, or Firm*—Bailey, Dority & Flint

[57] ABSTRACT

A crown release pressure tester for testing the pressure that is required for a crown carried on a container to fail or if the crown is leaking. The device includes an elongated housing which has a bore extending therethrough. The top portion of the container which has the crown that is to be tested threaded thereon is severed from the container and secured to the top of the housing in axial alignment with the bore. A piston threadably carried in the bore is rotated to increase the pressure imparted through liquid and compressed air until the crown releases from the top of the container. The pressure that the crown releases is recorded on a pressure gauge.

5 Claims, 5 Drawing Figures

CROWN RELEASE PRESSURE TESTER

BACKGROUND OF THE INVENTION

Heretofore, it has been required to routinely test containers such as soft drink containers, to determine the release or failure pressure of caps or crowns carried thereon. It is desirable that the crown release pressure be within certain tolerances so that it does not become a saftey hazard by exploding at high pressures yet the crown will withstand pressures encountered in carbonated beverages and the like.

One particular device utilized for testing the crowns of containers such as carried on plastic soft drink bottles is disclosed in U.S. Pat. No. 3,958,448. In this particular device, a needle is utilized for puncturing the crown and inserting a pressurized fluid into the container which is filled with its normal contents. The pressure applied to the bottle in one particular instance is supplied from an external pressurized source of air and it is allowed to build up until the crown releases or fails. Upon releasing of the crown the liquid flows out of the bottle. One problem with such a testing device is that it is quite messy as a result of the liquid flowing out over the testing apparatus. Another problem with such a device is that it normally has to be kept in a laboratory and as can be seen in the drawings, the crown that is being tested rests on a supporting pedestal during the tests. As a result of the external force applied through the pedestal the test would not be as accurate as if the crown and bottle were tested without any structure engaging the crown itself.

SUMMARY OF THE INVENTION

The present invention relates to a device for testing caps or crowns carried on containers and more particularly to a device for testing the release pressure of crowns carried on containers. The device includes an elongated housing which has a reduced diameter portion provided adjacent the top of the housing. Positioned on this reduced diameter portion is the top portion of the container which was previously severed from the container by means of a cutting tool. The top portion of the container is placed in alignment with an elongated bore extending through the housing. A piston is threadably carried within the bore. During the tests the bore is filled with a fluid allowing a small air gap to exist between the crown and the top level of the fluid. Upon rotating the piston, the pressure in the bore that is exerted upon the interior surface of the crown is gradually increased until the threads of the crown release from the threaded neck of the container. The pressure that the crown releases is recorded on a pressure gauge that is in communication with the bore extending through the housing.

When the crown releases only a very small amount of water it is expelled between the threads of the cap and the neck of the container as a result of filling the majority of the bore with liquid and leaving only a relatively small air gap between the surface of the liquid and the cap.

Accordingly, it is an important object of the present invention to provide a simple and effective device for testing to determine if a crown is properly applied to a container.

Another important object of the present invention is to provide a relatively small and portable device for testing crowns of containers and the like.

Still another important object of the present invention is to provide a simple, safe and sanitary device for testing to determine the failing pressure for crowns carried on articles such as soft drink containers and the like.

The construction designed to carry out the invention will be hereinafter described, together with other features thereof.

Another object of the present invention is to test the crowns placed on containers using rejected containers that have not been previously filled with product thereby not wasting a good container or product.

The invention will be more readily understood from a reading of the following specification and by reference to the accompanying drawings forming a part thereof, wherein an example of the invention is shown and wherein:

DESCRIPTION OF A PREFERRED EMBODIMENT

Figure 1:
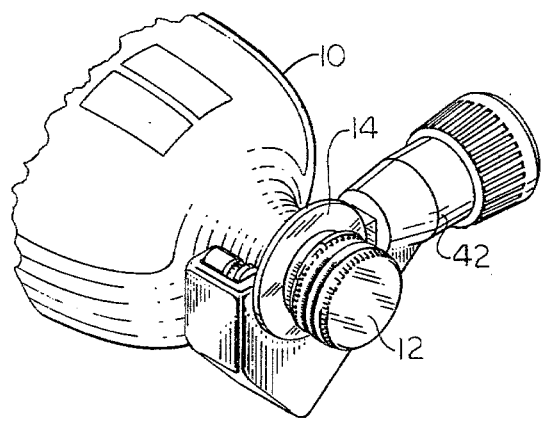
FIG. 1 is a fragmentary perspective view illustrating the top of a container being removed for testing.
Figure 2:
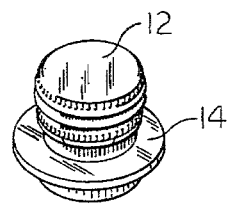
FIG. 2 is a perspective view illustrating the top of the container which is to be tested.
Figure 3:
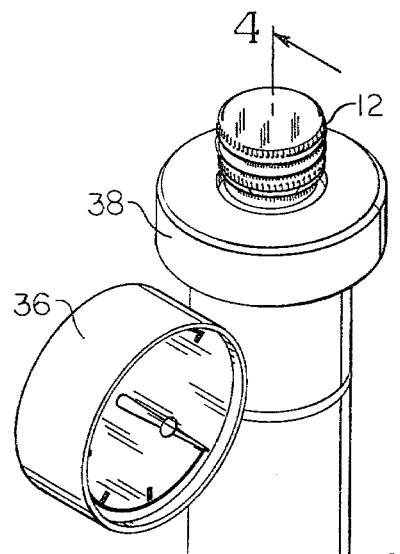
FIG. 3 is a perspective view illustrating a crown testing device constructed in accordance with the present invention.
Figure 4:
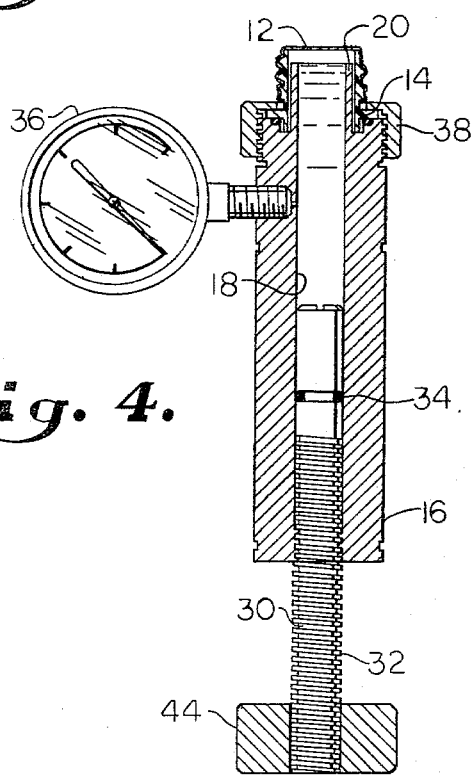
FIG. 4 is a sectional view taken along line 4—4 of FIG. 3.
Figure 5:
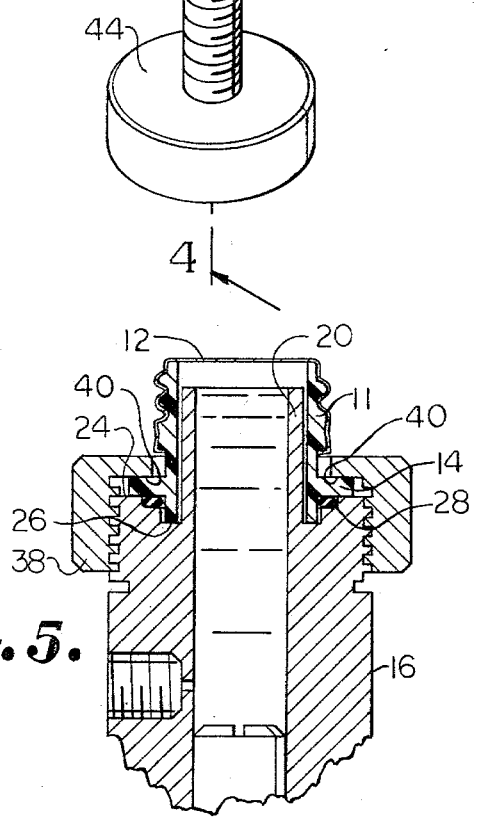
FIG. 5 is an enlarged sectional view showing the manner in which the top portion of the container is secured to the testing device.

Referring now more specifically to FIG. 1 of the drawing, there is illustrated a container 10 such as a plastic bottle which is commonly used as a package for soft drinks. The neck portion of the bottle 10 is threaded and has a standard rolled on aluminum crown 12 placed thereon. A radially extending flange 14 is provided adjacent the lower end of the neck 11 as best illustrated in FIGS. 4 and 5.

It is important to test the release pressure of the crowns 12 from a safety standpoint as well as an operational standpoint. It is important, of course, that the crown not rupture or fail prematurely to leak the contents out of the bottle as a result of normal pressure buildup inherent in carbonated drinks. Normally, when the crown releases, the gas and liquid carried in the bottle, escape between the threads carried on the neck 11 of the bottle and the threads provided on the crown 12. If the crown is not properly applied, it may pre-release as the crown is turned, allowing the crown to blow from the bottle sometimes with excessive speed. The test is made to check to make certain that the aluminum of the crown is rolled properly into the bottle grooves.

The testing device includes an elongated cylindrical housing 16 which has an elongated bore 18 extending axially therethrough. There is a reduced diameter portion 20 adjacent the top of the housing that extends downwardly to adjacent a circular horizontal flange 24. A circular groove 26 is interposed between the flange 24 and the bottom of the reduced diameter portion 20. A cylindrical O-ring 28 is carried on the flange 24 producing a sealing means between the flange 24 and the flange 14 carried on the neck of the bottle.

A piston 30 having threads 32 provided thereon is threadably carried in the lower portion of the elongated bore 18 and has an O-ring seal 34 carried on the upper end thereof providing a seal between the piston 30 and the inner wall of the elongated bore 18. Communicating with the elongated bore 18 is a pressure gauge 36 which is utilized for measuring the pressure within the bore 18.

The neck portion of the bottle being tested is secured to the top of the housing by means of a retaining collar 38 which is screwed on the top of the housing 16 with an inwardly projecting flange 40 thereof pressing against the top surface of the flange 14 carried on the neck of the bottle pressing the flange 14 flush against the O-ring 28 providing a seal therebetween.

When it is desired to test the pressure that a cap on a container will withstand or the pressure at which the cap or crown releases, first the top portion of the container is cut off using a conventional tube cutting device 42. The container being cut as shown in FIG. 1, is a conventional plastic bottle that is used for soft drinks. It is cut adjacent its neck so that the flange portion is retained on the top of the bottle. The elongated bore 18 is then substantially filled with water leaving a small gap approximately ⅛" adjacent the top thereof. The collar 38 is removed and the neck inserted over the reduced diameter tubular upper portion of the housing with the flange 14 pressing against the O-ring 28 providing a seal connection. The collar is then placed onto the top of the housing with the flange 40 of the collar pressing down on the upper surface of the flange 14 carried on the neck of the bottle.

The piston 30 is then rotated by means of the enlarged knob 44 causing the piston to rise within the bore 18. As the piston rises, the pressure within the elongated bore and on the inside of the crown 12 increases. The knob 44 is rotated until the cap 12 fails. When the cap 12 fails, normally the threads of the cap separate from the threads of the upper neck portion of the bottle allowing the air to escape therebetween. Since the liquid within the elongated bore is not compressed during the tests and only the air in the small air gap is compressed no dangerous explosive force is created during the test. Furthermore, as a result of the air gap being adjacent the top of the elongated bore 18 a natural pneumatic condition similar to that that would occur when the bottle is filled with a carbonated beverage is utilized in performing the tests.

As a result of the device being portable an operator can take the test device to the line on which the bottles are being run or into the trade area and perform the test with a minimum of mess from spilling of liquid.

While a preferred embodiment of the invention has been described using specific terms, such description is for illustrative purposes only, and it is to be understood that changes and variations may be made without departing from the spirit or scope of the following claims.

What is claimed is:

1. A crown release pressure tester for a container having a neck portion upon which said crown is placed for sealing said container, the neck portion and crown removed from said container, comprising:
   an elongated housing;
   an elongated bore provided in said housing;
   means for securing said removed neck portion with said crown provided thereon on a top portion of said housing with the interior of said crown in communication with one end of said elongated bore and said interior of said crown and said elongated bore being sealed from the atmosphere;
   a piston extending in said other end of said elongated bore;
   a seal provided between said piston and housing surrounding said bore; and
   means for moving said piston axially within said bore for gradually increasing the pressure on said crown for determining the pressure that said crown fails.

2. The crown release pressure tester as set forth in claim 1 further comprising:
   a pressure gauge communicating with said bore for registering the pressure that said crown failed.

3. The crown release pressure tester as set forth in claim 1 further comprising:
   internal threads carried in the wall of said elongated bore;
   threads carried on said piston meshing with said threads of said bore;
   said means for moving said piston axially within said bore including:
   (i) means for rotating said piston for gradually increasing the pressure within said bore and on said crown for determining the pressure that said crown fails.

4. The crown release pressure tester as set forth in claim 1 wherein said container to be tested is a plastic container having an elongated threaded neck upon which a crown is carried, and a radially extending flange carried adjacent a lower portion of said neck, said tester further comprising:
   a reduced diameter extension provided on said housing;
   said elongated bore extending through said reduced diameter extension;
   said means for securing said neck portion of said container on said housing including:
   (i) an internally threaded retaining collar, and
   (ii) threads carried on an upper portion of said housing;
   wherein when said neck portion is inserted on said reduced diameter extension and said retaining collar is screwed on said housing pressing said flange of said neck portion against said housing providing a seal between said elongated bore and said neck portion.

5. A device for testing to determine the amount of pressure that is required to rupture a threaded cap carried on the top of a container, and said top of said container being severed from said container, said device comprising:
   an elongated housing;
   a reduced diameter portion provided adjacent the top of said housing;
   an elongated bore extending through said housing and said reduced diameter portion;
   a piston threadably carried in a lower portion of said elongated bore;
   means providing a seal between said piston and the wall of said bore;
   means for securing said top of said container on said reduced diameter portion with the interior of said cap in communication with said elongated bore and said interior of said cap and said elongated bore being sealed from the atmosphere;
   a pressure gauge communicating with the interior of said bore; and
   means for rotating said piston increasing the pressure in said bore until the seal between said cap on the top of said container fails;
   whereby the pressure required to cause said cap to fail is registered on said pressure gauge.

* * * * *